United States Patent [19]

Hesselgren

[11] 4,339,279

[45] Jul. 13, 1982

[54] RETENTION COMPOSITION FOR DENTAL PROSTHESIS

[76] Inventor: Sven-Gunnar Hesselgren, Kummelvägen 19, S-161 39 Bromma, Sweden

[21] Appl. No.: 47,050

[22] Filed: Jun. 11, 1979

[30] Foreign Application Priority Data

Jun. 16, 1978 [SE] Sweden .................. 7806939

[51] Int. Cl.³ .................. A61K 5/00; C08L 1/26; C08L 3/02; C08L 5/00
[52] U.S. Cl. .................. 106/35; 106/194; 106/205; 106/209; 106/210; 106/214; 433/180
[58] Field of Search .................. 106/35, 205, 209, 210, 106/214, 194; 424/49; 433/180

[56] References Cited

U.S. PATENT DOCUMENTS

| | | | |
|---|---|---|---|
| 813,647 | 2/1906 | Haake .................. | 106/210 |
| 2,099,028 | 11/1937 | McCarthy .................. | 106/205 |
| 2,520,805 | 8/1950 | Joy .................. | 106/38.5 D |
| 2,756,874 | 7/1956 | Erickson et al. .................. | 106/38.5 D |
| 3,029,187 | 4/1962 | Steinhardt et al. .................. | 433/180 |
| 3,246,998 | 4/1966 | Higashi et al. .................. | 106/35 |
| 4,144,322 | 3/1979 | Cordon et al. .................. | 424/49 |
| 4,184,888 | 1/1980 | Zoumut .................. | 106/194 |

FOREIGN PATENT DOCUMENTS

| | | | |
|---|---|---|---|
| 762527 | 7/1971 | Belgium .................. | 433/180 |
| 650493 | 10/1962 | Canada .................. | 433/180 |

OTHER PUBLICATIONS

Chem. Abst. 84:126,058c, 1976.

*Primary Examiner*—Allan Lieberman
*Attorney, Agent, or Firm*—Lerner, David, Littenberg & Samuel

[57] ABSTRACT

The invention relates to a retention composition for dental prosthesis which, as well as the requisite retention agent, contains a compound inhibiting the growth of bacteria and fungi. The invention aims primarily at eliminating the problems of earlier inhibitors in such compositions which were found to produce toxic and allergic reactions in the mucous membrane tissues. According to the invention, said compound is sodium bicarbonate.

4 Claims, No Drawings

RETENTION COMPOSITION FOR DENTAL PROSTHESIS

BACKGROUND OF THE INVENTION

The present invention relates to a retention composition for dental prosthesis for application on those surfaces of the dental prosthesis which, when in position in the mouth, face the oral mucous membrane, in order to retain the dental prosthesis in position, said composition containing at least one orally acceptable retention agent which gives the composition the requisite properties for retention of the dental prosthesis, and a compound inhibiting the growth of bacteria and fungi.

Many wearers (about 50-65%) of removable dental prosthesis have trouble with their prosthesis to a greater or lesser extent. (Miller E. L., 1975, J. Dent. Assn. S.AFR. 30 (1): 89–93 and Budtz-Jörgensen E., 1978, JADA, 96, 96: 474–479). The trouble may manifest itself in different ways and the reasons may be various.

Keeping the prosthesis fixed in the intended position both during rest or relaxation and while speaking, talking but above all during movement connected with chewing, may be a problem for many people.

These inconveniences may appear even if the prosthesis is constructed in accordance with all the rules pertaining to dental artistry. The reason may be unalterable anatomic oral conditions which are unfavourable or other individual causes such as motoric insufficiency in the oral and jaw region. The latter is often the case with certain categories of people, such as old people and physically or mentally handicapped people. (Norderam E., 1977: Tandlakartidningen Vol. 69, No. 7). Inability to fix the prosthesis causes a feeling of insecurity in the individual and is often a psychological handicap in social contact with other people.

It is not unusual among denture wearers for inflammatory changes to occur in the oral mucous membrane against which the base of the prosthesis abuts. Through intensified research in this field it has now been established that the primary cause of such disease states is of microbial nature with the emphasis on the occurrence of fungi. The inflammatory conditions in the mucous membrane are thus often related to the occurrence of fungi in the base of the prosthesis itself, which is extremely difficult to overcome. (Budtz-Jörgensen E., 1974: Scan. J. Dent. Res. 82:151).

Various practical solutions have therefore previously been tried to eliminate the problems discussed above.

In order to improve the retention of the prosthesis it is extremely common to apply a fixing preparation containing adhesive or glue-like material, preferably sodium carboxy methyl cellulose, on the surface of the prosthesis facing the oral mucous membrane, normally termed the mucous membrane surface of the prosthesis. These fixing preparations usually consist of a powder which is applied onto the mucous membrane surface of the prosthesis and which comes into contact with the saliva-coated or saliva-producing mucous membrane, thereby forming a gel with adhesive action. Sometimes the prosthesis is moistened with some water before insertion into the mouth, in order to improve the gel formation. Fixing preparations are also available in the form of a paste which is prepared ready for use when it is manufactured. The gelling or adhesive agent of fixing preparations is generally sodium carboxy methyl cellulose.

The method described enables the wearer to improve the fixing of the prosthesis in a simple manner. For this reason it is often used. However, there are certain drawbacks, particularly if the composition is applied over a long period. The fixing preparation does not inhibit bacteria and fungus flora which normally exist in the oral cavity. Instead, as experience has shown, they may promote the chances of colonization for the microorganisms. Chemical inhibitors have been added to some types of fixing agents in order to prevent growth, but this has resulted in new problems. The continued use of such chemical inhibitors may easily produce toxic and allergic reactions in the mucous membrane tissues as a result of inhibitor exposure, particularly when the use is extended over a number of years of intermittent application.

Irrespective of whether the denture wearer uses retention composition or not, he must always perform a careful program of oral hygiene comprising daily cleansing of the prosthesis, mouth and any remaining teeth, in order to remove bacteria plaque which is being continuously produced, and the collection of food particles, the occurrence of which is difficult to prevent. (Hedegard E., 1977: Tandlakartidningen Vol. 69, No. 7). The omission of or insufficient prosthesis and oral hygiene may, apart from the more unpleasant feeling of bad odour and taste, give rise to a state of inflammation or even serious alternations in the mucous membrane, known as prosthesis stomatites, and caries attacks on the remaining teeth.

To clean the prosthesis as efficiently and gently as possible dentists recommend brushing with a soft brush and suitable chemical wetting agent, preferably having microbicidal properties. (Andrup B., 1977: Tandlakartidningen, Vol 69, No. 7 and Hesselgren S. G., 1973: Swed. Dent. J., Vol. 66:181).

As to the chemical cleansing there are a number of compositions available which are especially intended for prosthesis. Basically the cleansing composition consists of a combination of two or more chemical substances in powder or tablet form which, when dissolved in usual water, react with each other vigorously producing gas or bubbles ($CO_2$). It is this effervescing solution which is intended to automatically to remove the coating of bacteria plaque and remnants of fixing agent from the prosthesis when it is immersed in the solution, if successful without further mechanical cleansing.

SUMMARY OF THE INVENTION

The present invention eliminates first of all the risks of toxic or allergic action on the mucous membranes which were caused by the chemical fungus and bacteria inhibitors previously used. This is enabled due to the fact that the compound preventing the growth of bacteria and fungi essentially is or consists or sodium bicarbonate. By means of microbiological experiments it has been found that in water-soluble state sodium bicarbonate is an efficient inhibitor for the growth of bacteria and particularly for the growth of fungi which is so difficult to overcome. Without being limited to any theory, it is probably mainly the high pH value which causes this inhibition of growth. The growth of fungus is encouraged primarily in acid surroundings. The sodium bicarbonate thus replaces the bacteria inhibitors previously used which were in some respects harmful. The sodium bicarbonate may be included in an amount of from 10 to 90% by weight calculated on the composition.

It is unavoidable that small amounts of the retention composition applied or one or more of its constituents will be dissolved in the saliva in the oral cavity. However, it is not dangerous to swallow the component sodium bicarbonate in the amount occuring here. It is generally known that sodium bicarbonate is widely used for treating ordinary stomach troubles in considerably larger doses, without evidence of any negative side effects.

The appearance of inflammatory changes in the oral mucous membrane which is primarily caused by the occurence of fungi on the mucous membrane side of the prosthesis, is thus surprisingly counteracted by the use of a retention composition in accordance with the present invention containing sodium bicarbonate which, among other things, acts as an inhibitor for the growth of bacteria and fungi. The problems arising from the use of previously known chemical inhibitors described above are eliminated at the same time since the risk of toxic and allergic action on the mucous membranes is removed. The retention composition according to the invention can be used without interruption over a long period of time and need not in any case be replaced by one which should be free from chemical inhibitors. An additional advantage is obtained by the use of the sodium bicarbonate component in the retention composition. Thus, it is known that the remaining original teeth, are extremely prone to caries attack with the combined use of partial prosthesis. Since the caries process is characterised by an acid attack on the hard tissues of the teeth, the sodium bicarbonate which is released by the saliva, or where the retention agent is in direct contact with the dental surfaces, will serve as a buffer against a lowering of the pH value and will thus contribute to preventing caries.

As already mentioned, the retention composition according to the invention contains a retention agent which when the composition is applied, produces the requisite properties for the desired retention. This agent and/or a special, inert additive included therein, also acts as carrier for the sodium bicarbonate and thus as a depot for the sodium bicarbonate, from which depot a saturated solution will be continuously released. The retention agent can be generally defined as a fixing agent if by fixation is meant adhesive securing. Such a retention agent is sodium carboxy methyl cellulose which, in contact with an aqueous liquid or saliva, produces a sticky consistency with adhesive or glue-like properties. Other alkali metal salts of carboxy methyl cellulose can be used. As mentioned above, sodium carboxy methyl cellulose is a known retention agent in such compositions. Other known retention agents can be used, such as acacia rubber, dextrine and starch. Additives such as polyether and polyacrylates may be in included in the composition in order to reduce the solubility of the retention agent in water and control the consistency of the composition.

The invention also includes retention agents in quite a new class for the application in question. These new retention agents are based on salts of alginic acid which are insoluble or difficult to dissolve in water and which may be included in the composition as such or be formed in situ. Examples of such water-insoluble compounds are calcium alginate and lead alginate, the first of which is preferred. These are preferably produced in situ by introducing a water-soluble alginate into the composition, such as sodium, potassium, ammonium or magnesium alginate, preferably potassium alginate and sodium alginate, and a compound delivering a metal ion which produces the insoluble alginate, for instance calcium salt or lead salt. The calcium salts are preferred, particularly calcium sulphates which exist in various forms with varying degrees of solubility. The calcium sulphates are normally designated as difficult to dissolve. However, their solubility is sufficient for the purposes of the invention to enable calcium ions to dissolve and react with the alginic acid molecules. The calcium sulphate material exists in the form of anhydrite, $CaSO_4$; hemihydrate, $(CaSO_4)_2 \cdot H_2O$; and dihydrate, $CaSO_4 \cdot 2H_2O$. Of these the hemihydrate is preferred since it has the greatest solubility, namely 0.9 g/100 ml. In the presence of aqueous medium the calcium ions will replace sodium or potassium ions in the sodium or potassium alginate molecules in a cross-link which can be considered as a form of polymerisation. A composition according to the invention, containing an alginate-based retention agent has adhesive properties, unless a special additive is included to eliminate this adhesion. One such special additive is a filler in the form of kieselguhr which gives the composition a firmer, somewhat rubberlike elastic consistency, but which also has other favourable effects.

In view of the above, the composition according to the invention, besides sodium bicarbonate, may include a retention agent corresponding to or substantially corresponding to the known alginate-based materials generally designated "dental impression compounds", which are used for impressions of teeth and surrounding tissue. When a mixture according to the invention of such alginate-based impression material and sodium bicarbonate is brought into contact with aqueous medium, such as saliva, a somewhat firmer, slightly rubberlike elastic consistency is obtained. When such a retention agent is applied on the prosthesis, a filmlike layer is formed between mucous membrane and the base of the prosthesis, which is easy to remove in larger pieces and which can be caused to flake off as will be described in more detail in the following. Since such a layer has a somewhat firmer consistency and lasts longer than a layer of carboxy methyl cellulose or similar substance, since it is not dissolved by saliva so quickly as a retention composition containing only carboxy methyl cellulose, it is obtained in a simple manner what is known in odontology as a temporary re-basing of the prosthesis. This is particularly desirable if the fit of the prosthesis against the support surface has altered with time and become unsatisfactory, but the alteration has not gone so far that a permanent re-basing must be performed by the dentist. The wearer of the prosthesis can thus easily perform this adjustment without having to visit the dentist.

Although at least initially there is a certain amount of adhesion in a composition based on a dental impression material, the retention of the prosthesis is attributed primarily to the improved sealed which is effected with the firmer rebasing agent produced by the alginate material, particularly at the edges of the prosthesis in conjunction with the transition between the firmer mucous membrane in the gum and the softer mucous membrane of the cheek. The plastic consistency of the alginate provides optimum fit in these regions after insertion of the prosthesis, a fit which will remain for a considerable time due to its conversion to an elastic, firmer consistency through the solidification process (during which insoluble alginate is formed). Contrary to the alginate composition carboxy methyl cellulose lacks this ability.

If increased adhesion is desired, an additional retention agent such as sodium carboxy methyl cellulose can be used in the alginate composition. The proportions of the three main components may in this case be within the following ranges: 10-50% by weight of sodium bicarbonate, 20-60% by weight of sodium carboxy methyl cellulose and 20-60% by weight of alginate-based dental impression material.

Another aspect of the present invention is based on a retention composition containing an alginate salt or producing an alginate salt according to the above and which contains or is free from sodium bicarbonate or other inhibitors.

The invention is illustrated further in the following by means of some examples. However, these are not limiting to the invention.

EXAMPLE 1

|  | Composition, % by weight | | |
| --- | --- | --- | --- |
|  | I | II | III |
| Sodium carboxy methyl cellulose | 50 | 25 | 75 |
| Sodium bicarbonate | 50 | 75 | 25 |
|  | 100 | 100 | 100 |

The retention compositions according to the three formulations were produced by mixing the two constituents in powder form to obtain a homogenous mixture. The constituents are preferably in the form of particles lying within approximately the same range of average particle size.

EXAMPLE 2

|  | Parts by weight |
| --- | --- |
| Sodium carboxy methyl cellulose | 1 |
| Sodium bicarbonate | 1 |
| Dental impression material | 1 |

The impression material consists of a powder mixture containing 14% by weight of potassium alginate, 74% by weight of kieselguhr and 12% by weight of calcium sulphate, dihydrate.

The powder composition selected within the limits specified is dependent on the consistency desired in the retention composition when used in the mouth. More carboxy methyl cellulose will give a stickier mixture, whereas increasing the alginate component will result in a firmer prosthesis support with good fit at the edge but a less sticky consistency.

The three main constituents in the above formulations were mixed to a homogenous powder composition which was then applied as follows:

The previously cleaned mucous membrane side of the dental prosthesis was powdered with the described powder composition, a thin layer being spread over the entire surface. The powdered surface was then slightly moistened with a few drops of water and inserted in the mouth of a patient. As the powder mixture was converted to gel form upon contact with the saliva in the oral cavity, the adhesion of the prosthesis to the surface below increased so that a comfortable feeling of stabilization was gradually experienced by the patient.

Another way of preparing the retention agent is to incorporate glycerine or some other such inert agent controlling the consistency in such an amount that, together with the powder, it produces a pastelike product which then forms the intended retention agent upon use, through contact with water or saliva in accordance with the chemical reactions described earlier.

Microbiological experiments have been performed to determine growth inhibition and these experiments are described in the following.

EXPERIMENT 1

To a number of test tubes containing 10 ml broth for bacteria cultivation (nutrient broth, Difco) it was added 0.8 g sodium bicarbonate (saturated solution), after which one drop of a pure culture of fungus (Candida Albicans), 24-hours old, was innoculated in each. Cultivation was then carried out at 37° C. for three days. In no case could any growth be established. However, a corresponding number of control experiments performed without the addition of sodium bicarbonate all showed growth.

EXPERIMENT 2

Similar experiments as described above were also performed with innoculation of fresh saliva. The results agreed with those obtained in the above experiments with fungus, i.e. no growth was noted.

The use of a retention composition according to the present invention gives the important additional improvement that sodium bicarbonate remaining on the dental prosthesis can act as a subsequent reaction agent when it is brought to reactwith an acid or an acidified cleaning agent dissolved in water, for instance. This means that the cleaning composition can be made cheaper tha the conventional compositions since it is unnecessary to have any latent reaction agent for the acid in the cleaning composition.

The cleaning liquid may consist only of an acid, such as acetic acid for use in the household or by dissolving a suitable amount of a cleaning composition in water, said composition containing an acid, for instance citric acid, as main component, plus suitable detergents. When the prosthesis is then immersed in this acid solution there will be a chemical reaction with strong foaming between the remaining depot of sodium bicarbonate on the prosthesis base and the acid in the water solution so that the retention mass is gradually loosened from the surface of the prosthesis as long as there is an excess of acid. It will be understood that the proportions of alkali and acid can easily be adjusted so that the entire content of sodium bicarbonate in the retention mass is consumed. The prosthesis is thus completely freed from the sticky coating in which the sodium bicarbonate is incorporated.

The cleaning composition used may contain strong chemical inhibitors for disinfection and may, as mentioned above, be supplemented by surface-active agent to further improve the cleaning effect. In such cases the prosthesis should be rinsed in running water after the chemical cleaning procedure, thus removing all substances which are damaging to the mucous membrane, before returning the prosthesis to the mouth after repowdering it with retention powder for retention or adhesion, etc. The hygiene program described should be performed every evening or more often if required, or in accordance with instructions from a dentist.

I claim:

1. A retention composition for dental prosthesis for application between the surfaces of the dental prosthesis and oral mucous membrane of the mouth of a subject such that said retention composition retains said dental prosthesis in position in the mouth, said retention composition consisting essentially of (1) an effective amount of an orally acceptable retention agent to provide sufficient adhesive characteristics to said composition to maintain said dental prosthesis in position in the mouth, said retention agent being selected from the group consisting of an alkali metal salt of carboxy methyl cellulose, acacia, dextrine, starch, and mixtures thereof, and (2) an effective amount of sodium bicarbonate to inhibit the growth of bacteria and fungi.

2. A retention composition according to claim 1 wherein said retention agent is a sodium salt of a carboxy methyl cellulose.

3. A retention composition according to claim 1 wherein said sodium bicarbonate is present in an amount of from 10 to 90% by weight of the composition.

4. A retention composition according to claim 1 wherein the retention agent is an alkali metal salt of carboxy methyl cellulose.

* * * * *

Notice of Adverse Decision in Interference

In Interference No. 101,449, involving Patent No. 4,339,279, S.-G. Hesselgren, RETENTION COMPOSITION FOR DENTAL PROSTHESIS, final judgment adverse to the patentee was rendered Dec. 9, 1985, as to claims 1–4.
[*Official Gazette February 11, 1986.*]